US007309318B2

(12) United States Patent  
Cassell et al.

(10) Patent No.: US 7,309,318 B2
(45) Date of Patent: Dec. 18, 2007

(54) FLEXIBLE COMPOSITE GUIDEWIRE FOR INTRAVASCULAR CATHETER

(75) Inventors: Robert Cassell, Otsego, MN (US); Jeffrey H. Vogel, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/246,271

(22) Filed: Sep. 18, 2002

(65) Prior Publication Data

US 2004/0054301 A1    Mar. 18, 2004

(51) Int. Cl.
*A61B 5/00*     (2006.01)
*A61M 25/00*   (2006.01)

(52) U.S. Cl. ..................................... 600/585
(58) Field of Classification Search ................ 600/585; 604/525, 527, 530, 526, 523, 96.01; 385/105; 174/108; 264/1.28
See application file for complete search history.

(56) References Cited

U.S. PATENT DOCUMENTS

| 2,221,138 | A | 11/1940 | Hendrickson | |
|---|---|---|---|---|
| 3,612,058 | A | 10/1971 | Ackerman | |
| 4,257,421 | A | 3/1981 | Beal | |
| 4,345,602 | A | 8/1982 | Yoshimura et al. | |
| 4,504,268 | A | 3/1985 | Herlitze | |
| 4,657,024 | A | 4/1987 | Coneys | |
| 4,841,976 | A | 6/1989 | Packard et al. | |
| 4,867,174 | A | 9/1989 | Skribiski | |
| 4,932,419 | A | 6/1990 | de Toledo | |
| 5,052,404 | A | 10/1991 | Hodgson | |
| 5,103,543 | A | 4/1992 | Hodgson | |
| 5,154,705 | A * | 10/1992 | Fleischhacker et al. | ..... 604/526 |
| 5,230,033 | A * | 7/1993 | Soodak | ........ 385/105 |
| 5,251,640 | A | 10/1993 | Osborne | |
| 5,357,979 | A | 10/1994 | Imran | |
| 5,423,771 | A | 6/1995 | Imran | |
| 5,514,128 | A | 5/1996 | Hillsman et al. | |
| 5,827,201 | A * | 10/1998 | Samson et al. | ............. 600/585 |
| 5,897,819 | A | 4/1999 | Miyata et al. | |
| 5,910,364 | A | 6/1999 | Miyata et al. | |
| 5,951,494 | A | 9/1999 | Wang et al. | |
| 5,971,975 | A * | 10/1999 | Mills et al. | ................. 604/527 |
| 6,019,736 | A | 2/2000 | Avellanet et al. | |
| 6,165,140 | A | 12/2000 | Ferrera | |
| 6,175,669 | B1 | 1/2001 | Colston et al. | |
| 6,217,567 | B1 * | 4/2001 | Zadno-Azizi et al. | ........ 604/530 |
| 6,251,085 | B1 | 6/2001 | Tezuka | |
| 6,280,539 | B1 | 8/2001 | Abrams et al. | |
| 6,340,441 | B1 | 1/2002 | Meyer et al. | |
| 6,673,025 | B1 * | 1/2004 | Richardson et al. | ......... 600/585 |

FOREIGN PATENT DOCUMENTS

JP          01062172 A  *  3/1989

* cited by examiner

*Primary Examiner*—Max F. Hindenburg
*Assistant Examiner*—Brian Szmal
(74) *Attorney, Agent, or Firm*—Crompton, Seager & Tufte LLC

(57) ABSTRACT

The present invention relates generally to guidewires with a high level of torquability, flexibility, and elasticity. In an embodiment, a guidewire comprises an elongate shaft having an outside diameter. The shaft may include a filler and a polymeric matrix, wherein the filler includes a plurality of wires, wherein the matrix substantially surrounds the filler, and wherein the outside diameter of the shaft is sized appropriately for being disposed within a lumen of an intravascular catheter.

35 Claims, 3 Drawing Sheets

US 7,309,318 B2

FLEXIBLE COMPOSITE GUIDEWIRE FOR INTRAVASCULAR CATHETER

FIELD OF THE INVENTION

The present invention pertains to guidewires for use with intravascular catheters. More particularly, the present invention pertains to guidewires with a desired level of flexibility, torquability, and pushability.

BACKGROUND OF THE INVENTION

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

Intravascular catheters are commonly used in conjunction with a guidewire. A guidewire may be advanced through the patient's vasculature until it has reached a target location. Once in place, a catheter may be threaded onto the guidewire and urged distally until the distal end of the catheter reaches a target location.

SUMMARY OF THE INVENTION

The present invention pertains to a refinement to guidewires, for example, improved pushability, flexibility, and torquability.

In one embodiment, the guidewire shaft is comprised of a polymeric matrix and a filler or a plurality of wires.

DETAILED DESCRIPTION OF THE EMBODIMENTS

Figure 1:
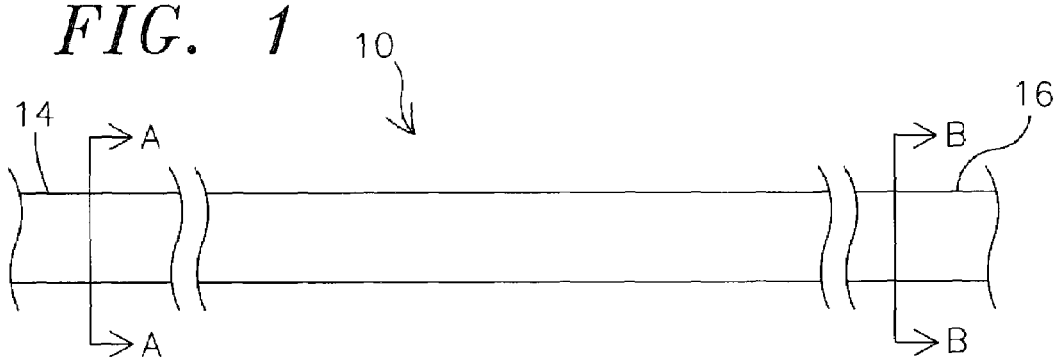
FIG. 1 is a side view of a portion of a guidewire shaft according to an embodiment of the invention.

The following description should be read with reference to the drawings wherein like reference numerals indicate like elements throughout the several views. The detailed description and drawings represent select embodiments and are not intended to be limiting.

FIG. 1 is a side view of a portion of a guidewire shaft 10 according to an embodiment of the invention. Guidewire shaft 10 includes a proximal end 14 and a distal end 16. Guidewire shaft 10 is adapted to pass through a lumen of a catheter. For example, a guide catheter may be steered to a target region through the vasculature, guidewire shaft 10 may be threaded through a lumen of the guide catheter, and a catheter (e.g., a therapeutic catheter) may be passed over the guidewire. The therapeutic catheter may be an angioplasty catheter, an atherectomy catheter, an intravascular catheter, etc.

In order to fully appreciate the many differing embodiments of guidewire shaft 10, it may be helpful to look at guidewire shaft 10 in a plurality of cross sectional views. For example, a cross section through line A-A may include a schematic view of guidewire shaft 10 proximate proximal end 14. Similarly, a cross section through line B-B may include a schematic view of guidewire shaft 10 distal end 16. FIGS. 2-6 are examples of cross sectional views, including views through lines A-A and B-B.

Figure 2:
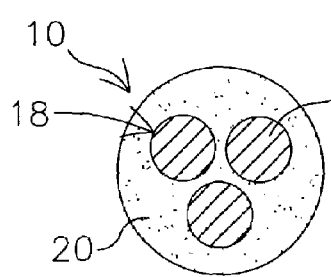
FIG. 2 is a schematic cross sectional representation of a guidewire shaft.

FIG. 2 is a cross sectional representation of guidewire shaft 10 according to an embodiment of the invention taken at A-A on FIG. 1. Guidewire shaft 10 may comprise a filler 18 encompassed by a matrix 20. Filler 18 may comprise a plurality of wires 22. According to an embodiment, the recitation of the term wire is intended to describe an elongate element appropriate for multiple embodiments of the current invention. Therefore, a wire may be understood to include a number of shapes, sizes, and configurations without departing from the spirit of the invention.

Wires 22 may be comprised of materials including, but not limited to, metals, stainless steel, nickel alloys, nickel-titanium alloys, thermoplastics, high performance engineering resins, fluorinated ethylene propylene (FEP), polymer, polyethylene (PE), polypropylene (PP), polyvinylchloride (PVC), polyurethane, polytetrafluoroethylene (PTFE), polyether block amide (PEBA), polyether-ether ketone (PEEK), polyimide, polyamide, polyphenylene sulfide (PPS), polyphenylene oxide (PPO), polysufone, nylon, perfluoro (propyl vinyl ether) (PFA), glass, carbon fibers, aramid fibers, Kevlar®, Spectra®, and combinations thereof. Individual wires may comprise differing materials. For example, a first wire may be comprised of metal and a second wire may be comprised of a polymer. In addition, the composition of individual wires may change along the length of an individual wire. For example, a distal portion of a first wire may be comprised of a polymer and a proximal portion of the wire may be comprised of metal.

Wires 22 making up filler 18 may be arranged in a number of differing configurations. For example, wires 22 may extend parallel to one another along the length of guidewire shaft 10. According to this embodiment, parallel is understood to include approximately parallel, partially parallel, or generally aligned lengthwise. Alternatively, wires 22 may be twisted, layer, wrapped, or braided with one another. In a second alternative, wires 22 may have a differing configuration along the length of guidewire shaft 10. For example, wires 22 may include regions where they extend parallel to one another and regions where wires 22 are intertwined.

The number of wires 22 appropriate for multiple embodiments of the invention may vary. It is anticipated that any number of wires 22 may be used so long as guidewire shaft 10 maintains a width (i.e., outside diameter) that is appropriate. Moreover, differing wires 22 may span differing lengths of guidewire shaft 10. For example, an individual wire may be truncated near a distal end of guidewire shaft 10. This embodiment may be particularly useful where it may be desirable for guidewire shaft 10 to have a decreased outside diameter (e.g., near a distal end) or altered flexibility.

It is believed that if a plurality of wires 22 are used to form a guidewire, the resiliency of the resultant structure could approach that of the individual wires 22. Accordingly, it is believed that the use of filler 18 in accordance with an embodiment of the invention may result in guidewire shaft 10 having increased resiliency pushability, flexibility and torsional stiffness.

Matrix 20 may encompass filler 18 along the length of guidewire shaft 10. Matrix 20 may serve primarily as a means for holding wires 22 together as well as contributing to the stiffness and buckling strength of guidewire shaft 10. The proportion of matrix 20 relative to total cross sectional area of shaft 10 may vary. In some embodiments, matrix 20 may constitute less than a majority of the cross sectional area of guidewire shaft 10. For example, matrix 20 may contribute up to about 50% of the cross sectional area. In other embodiments, matrix 20 may contribute less of the total cross sectional area. For example, in some embodiments matrix 20 may constitute up to about 10-20% or up to about 5% of the cross sectional area. Alternatively, matrix 20 could constitute a larger portion of the area (including the majority of the area).

Matrix 20 may comprise a curable adhesive, an ultraviolet-curable adhesive, an epoxy, an elastomer, and combinations thereof. Alternatively, matrix 20 may be comprised of materials similar to those listed above including polymers.

The composition of matrix 20 may vary along the length of guidewire shaft 10. For example, matrix 20 may comprise a relatively rigid polymer proximate proximal end 20 and a relatively flexible polymer near distal end 16. The transition may be smooth (i.e., a gradual change in durometer, stiffness, flexibility, etc.) or it may be stepwise.

Matrix 20 may be coupled to filler 18 in a number of ways. For example, matrix 20 may be extruded onto wires 22 through a die. Other manufacturing and molding techniques may be used to couple filler 18 with matrix 20. A person of ordinary skill in the art would be familiar with differing manufacturing techniques appropriate for coupling matrix 20 and filler 18 according to multiple embodiments of the invention.

Figure 3:
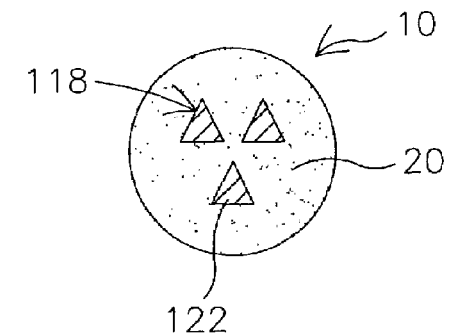
FIG. 3 is an alternate schematic cross sectional representation of a guidewire shaft having non-circular wires.

FIG. 3 is an alternate schematic cross sectional representation of a guidewire shaft 10 having non-circular wires 122 according to an embodiment of the invention taken at A-A on FIG. 1. In addition to the use of wires having a circular cross section, filler 118 may include wires 122 having a cross section that is non-circular. For example, the cross section of wires 122 may be non-circular shapes including, but not limited to, square, rectangular, triangular, oval, trapezoidal, pie-shaped, hexagonal, ribbon, irregular shapes, regular shapes, geometric shapes, etc. In addition, the shapes of individual wires need not be identical. For example, a particular filler 118 may include a first wire that has a cross section that is circular and a second wire with a cross section that is non-circular (e.g., rectangular).

Figure 4:
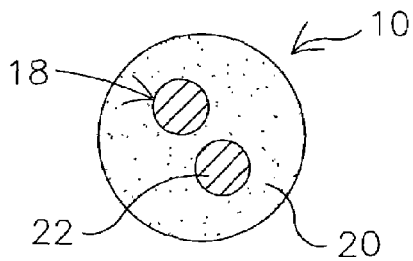
FIG. 4 is an alternate schematic cross sectional representation of a guidewire shaft near the distal end, wherein some of the wires are truncated.

FIG. 4 is an alternate schematic cross sectional representation of a guidewire shaft 10 taken at B-B on FIG. 1, wherein some of the wires are truncated. Wires 22 may extend along the length of guidewire shaft 10 from proximal end 14 to distal end 16. In an embodiment, some of wires 22 may be truncated such that they extend from proximal end 20 to a location proximal of distal end 16. This truncation may lead to increased flexibility. Truncation of some of wires 22 is depicted in FIG. 3 as the absence of some of wires 22. Truncation may occur proximate distal end 16.

Figure 5:
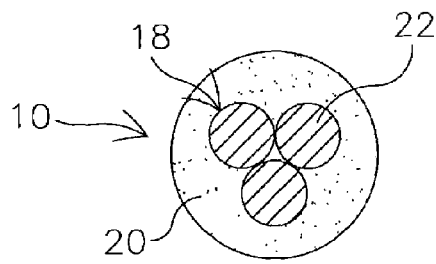
FIG. 5 is an alternate schematic cross sectional representation of a guidewire, wherein individual wires are closely associated.

FIG. 5 is an alternate schematic cross sectional representation of a guidewire shaft 10, wherein individual wires 22 are more closely associated than in FIG. 2. Describing wires 22 as being closely associated is understood to mean that wires 22 are relatively close to one another, tightly associated, or in close proximity. The relative proximity of individual wires 22 may vary along the length of guidewire shaft 10.

According to this embodiment, as wires 22 become more closely associated, the guidewire becomes more flexible and resilience. In an exemplary embodiment, wires 22 are more closely associated near distal end 16 than at proximal end 14 and, thus, may increase the flexibility of guidewire shaft 10 near distal end 16. According to this embodiment, the cross section shown in FIG. 5 may be taken through line B-B.

Alternatively, it may be desired to manufacture guidewire shaft 10 with wires 22 more closely associated near proximal end 14. In order to achieve the objects of this embodiment, matrix 20 may need to be manufactured to have differing physical properties along the length of guidewire shaft 10. For example, matrix 20 may be relatively rigid near proximal end 14 and relatively flexible near distal end 16. According to this embodiment, it may be necessary for matrix 20 to have increased durometer (or similar physical properties) so as to allow guidewire shaft 10 to maintain the desired level of stiffness near proximal end 14. According to this embodiment, the position of filler 18 relative to matrix 20 may be altered without alteration of the outside diameter of guidewire shaft 10. Alternatively, the outside diameter of guidewire shaft 10 may be altered due to changes in proximity of wires 22. For example, guidewire shaft 10 may taper near distal end 16 of elongate shaft 12.

Figure 6:
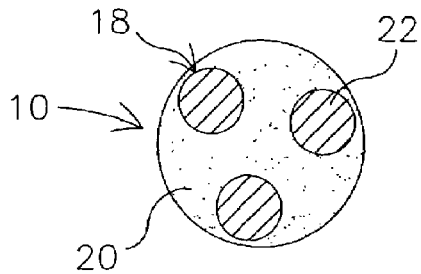
FIG. 6 is an alternate schematic cross sectional representation of a guidewire, wherein individual wires are less closely associated.

FIG. 6 is an alternate schematic cross sectional representation of a guidewire shaft 10, wherein individual wires 22 are less closely associated than in FIG. 2. It is believed that by less closely associating wires 22, the relative flexibility of guidewire shaft 10 may decrease. According to this embodiment, individual wires 22 may be less closely associated (i.e., less close to one another), for example at proximal end 14. Therefore, FIG. 6 may represent a cross section taken through line A-A. Accordingly, it may be useful to manufacture guidewire shaft 10 with wires 22 less closely associated near proximal end 14.

Figure 7:
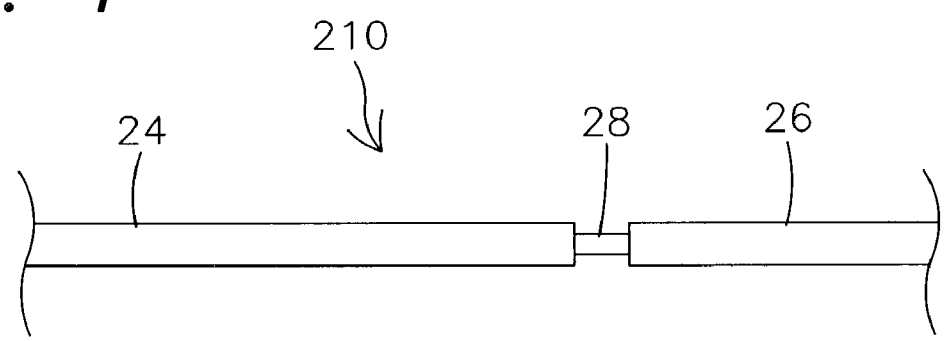
FIG. 7 is a view of a guidewire according to an embodiment of the invention.

FIG. 7 is a plan view of a guidewire 210 according to an embodiment of the invention. Guidewire 210 may comprise a proximal region 24, a distal region 26, and a linking region 28. According to this embodiment, proximal region 24 may comprise an elongate stainless steel or nickel-titanium alloy mandrel. Alternatively, proximal region 24 may comprise any number of materials that are generally stiff.

Distal region 26 may be comprised of an elongate shaft (e.g., guidewire shaft 10 having filler 18 encompassed by matrix 20) similar to what is disclosed above. The combination of a relatively flexible distal region 26 with a relatively stiff proximal region 24 may result in guidewire 210 having the desired level of pushability, torquability, and flexibility.

Linking region 28 may couple proximal region 24 to distal region 26 by adhering to opposite ends thereof. Linking region 28 may be comprised of inconel, nickel-chromium alloy, nickel-chromium-iron alloy, or another alloy suitable for coupling proximal region 24 to distal region 26. Alternatively, linking region 28 may be comprised of materials similar to those listed above including polymers.

Figure 8:
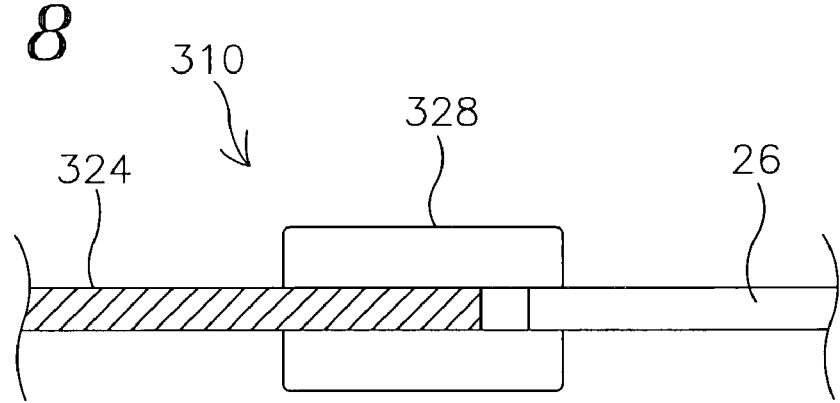
FIG. 8 is a view of an alternate guidewire according to an embodiment of the invention.

FIG. 8 is a plan view of an alternate embodiment of a guidewire 310 according to an embodiment of the invention. Guidewire 310 may comprise a proximal region 324, distal region 26, and a linking region 328. Linking region 328 may couple proximal region 324 to distal region 26. For example, linking region 328 may comprise a polymeric member that can be disposed over opposite ends of proximal region 324 and distal region 26 so as to substantially couple said regions. A number of differing shapes, configurations, and materials may be used for linking region 328 without departing from the spirit of the invention.

Figure 9:
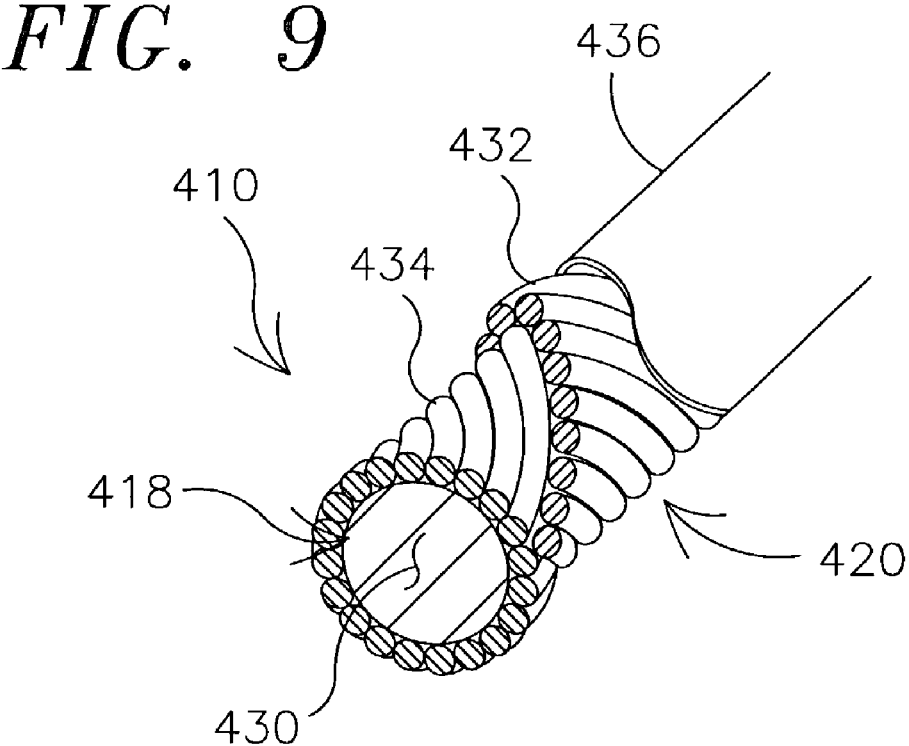
FIG. 9 is a partially cutaway perspective view of an alternate guidewire according to an embodiment of the invention.

FIG. 9 is a partially cutaway perspective view of an alternate guidewire 410 according to an embodiment of the invention. Guidewire 410 may include filler 418 that includes a core member 430. Core member 410 can comprise a generally solid metallic shaft. Suitable materials for core member 410 include stainless steel, a nickel-titanium alloy, a polymer, etc.

Guidewire 410 also includes a matrix 420. Matrix 420 may include a first bundle 432 and a second bundle 434 generally disposed about core member 430. Matrix 420 may also include an outer sheath 436. In some embodiments, first bundle 432 and/or second bundle 434 are comprised of a plurality of polymeric or metallic wires. For example, bundles 432/434 (or more generally matrix 420) can be made from various performance grades of polyether block amide (PEBA). Some of bundles 432/434 may also contain an amount of liquid crystal polymer (LCP), for example XYDAR® OR VECTRA®, blended therein to increase torqueability. In order to modify the performance (e.g., flexibility) of bundles 432/434, property-enhancing additives may be blended with the PEBA in order to achieve the desired performance characteristics for the individual bundles 432/434. In addition to or independently of including LCP, matrix 420 may also include polyester, polycarbonate, nylon, polyetherimide, or other suitable materials. It can be appreciated that the number of wires or the material composition of the wires can be varied without departing from the spirit of the invention. For example, first bundle 432 may comprise one set of wires being comprised of a polymer and one set of wires being comprised of a metal (i.e., intra-bundle variation of fibers). Additionally, the materials used for first bundle 432 may differ from those of second bundle 434 (inter-bundle variation).

First bundle 432, second bundle 434, or both may be twisted about core member 430 to alter the physical properties of guidewire 410 (e.g., increase torquability). In some embodiments, first bundle 432 and second bundle 434 are twisted about core member in different directions (e.g., one bundle twisted in a clockwise direction and the other in a counter-clockwise direction). In embodiments where first bundle 432 and second bundle 434 are both twisted in the same general direction, second bundle 434 may be skewed about 45° relative to first bundle 434 or more. However, it can be appreciated that the direction of twisting and the amount of skew (including no skew) between bundles 432/434 can be altered in different embodiments of the invention.

The flexibility of guidewire 410 may also be altered by altering the orientation of bundles 432/434. For example, tightening the pitch of either bundle 432/434 may decrease the flexibility. The pitch may be tightened, for example, by tightening the twisting of bundles 432/434 relative to one another or to core member 430.

Manufacturing of guidewire 410 may, for example, include one or more extrusion steps. For example, core member 430 may comprise a solid metal shaft and bundles 432/434 may be sequentially extruded over core member 430. Extrusion generally disposes bundles 432/434 about core member 430 in a generally helical fashion. Separate extrusion steps may be utilized to orient first bundle 432 about core member 430 in a first direction and second bundle 432 in a second direction. In some embodiments, the first direction and the second direction are different. However, first direction and second direction may be the same. In alternative embodiments, bundles 432/434 may be passed through one or more extrusion dies, including crosshead dies. According to this embodiment, the extrusion dies may be changed during an individual or set of extrusion steps. In another embodiment, extrusion may include the use of a rotating extrusion head.

Extrusion may allow further variations in the properties of matrix 420. For example, extrusion may allow the density or durometer to be varied within bundles 432/434. Altering the durometer may be beneficial because often it is desirable to manufacture guidewire with enhanced distal flexibility. Thus, extrusion may allow the durometer of bundles 432 and/or 434 to be decreased in the distal direction in order to increase distal flexibility.

Figure 10:
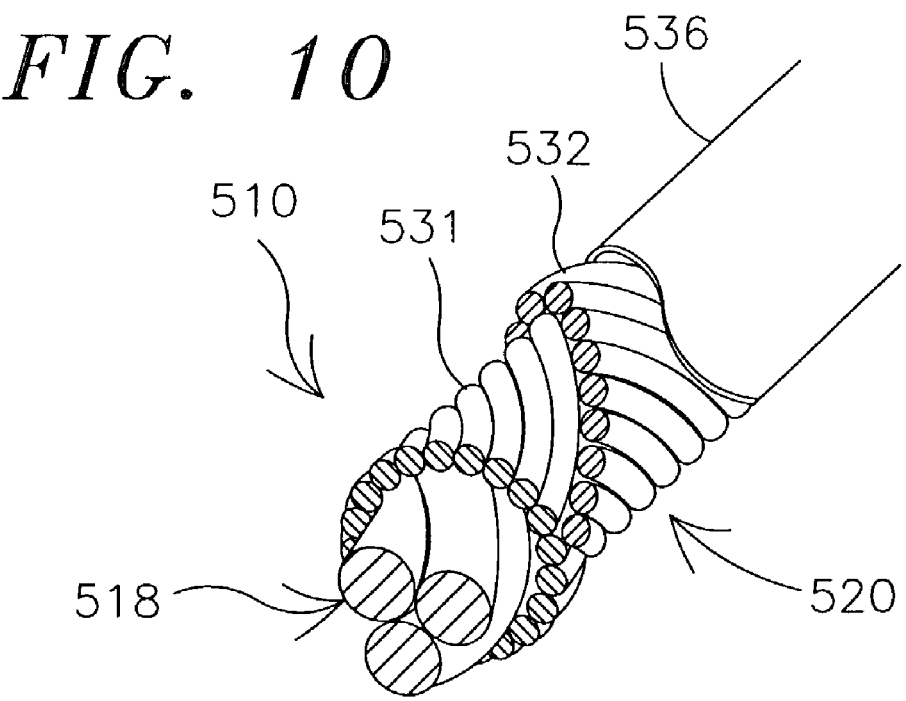
FIG. 10 is a partially cutaway perspective view of an alternate guidewire according to an embodiment of the invention.

FIG. 10 is a partially cutaway perspective view of an alternate guidewire 510 according to an embodiment of the invention. Guidewire 510 is essentially the same in form and function as guidewire 410 except that filler 518 comprises a twisted core member 530. According to this embodiment, core member 530 may comprise one or more wires that are twisted about one another. Similar to what is described above, the materials (e.g., metals, polymers, etc.) and number of wires making up core member 530 (as well as matrix 520, first bundle 532, second bundle 534, and outer sheath 536) may be varied. Guidewire 510 may also be manufactured similarly to guidewire 410.

It should be understood that the above disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An intravascular guidewire shaft having a first region and a second region, comprising:
   a first wire;
   a second wire twisted about the first wire, and the first wire is twisted about the second wire;
   a matrix, wherein the first wire and the second wire are substantially encompassed by the matrix;
   wherein the matrix has a proximal section having a first flexibility and a distal section having a second flexibility different from the first flexibility; and
   wherein the second wire is more closely associated with the first wire in the first region than in the second region.

2. The guidewire in accordance with claim 1, wherein the first wire has a cross section that is circular.

3. The guidewire in accordance with claim 1, wherein the first wire has a cross section that is non-circular.

4. The guidewire in accordance with claim 1, wherein the first wire is truncated.

5. The guidewire in accordance with claim 1, wherein the first wire and the second wire are braided.

6. The guidewire in accordance with claim 1, wherein the first wire is comprised of stainless steel.

7. The guidewire in accordance with claim 1, wherein the first wire is comprised of glass.

8. The guidewire in accordance with claim 1, wherein the first wire is comprised of a polymer.

9. The guidewire in accordance with claim 1, wherein the first wire is comprised of carbon fibers.

10. The guidewire in accordance with claim 1, wherein the matrix is comprised of adhesive.

11. The guidewire in accordance with claim 1, wherein the adhesive is ultraviolet-curable.

12. The guidewire in accordance with claim 1, wherein the matrix is comprised of epoxy.

13. The intravascular guidewire shah of claim 1, wherein the proximal section of the matrix is stiffer than the distal section of the matrix.

14. The intravascular guidewire of claim 1, wherein the first region of the guidewire shaft is a proximal region and the second region of the guidewire shaft is a distal region.

15. The intravascular guidewire of claim 1, wherein the first region of the guidewire shaft is a distal region and the second region of the guidewire shaft is a proximal region.

16. An intravascular guidewire shaft, comprising:
a first wire;
a second wire twisted about the first wire, and the first wire is twisted about the second wire;
a matrix, wherein the first wire and the second wire are substantially encompassed by the matrix;
wherein the first wire has a length and wherein the material composition of the first wire changes along the length; and
wherein the second wire is more closely associated with the first wire in the first region than in the second region.

17. The intravascular guidewire shaft of claim 16, wherein the first wire has a proximal section and a distal section and wherein the distal section includes a polymer.

18. The intravascular guidewire shaft of claim 17, wherein the proximal section includes a metal.

19. An intravascular guidewire, comprising:
an elongate shaft having an outside diameter;
wherein the shaft includes a filler and a polymeric matrix;
wherein the filler includes a plurality of wires;
wherein the matrix substantially surrounds the filler;
wherein the matrix includes an ultraviolet-curable adhesive;
wherein the matrix has a proximal section having a first flexibility and a distal section having a second flexibility different from the first flexibility; and
wherein the outside diameter of the shaft is sized appropriately for being disposed within a lumen of an intravascular catheter;
wherein the plurality of wires are more closely associated with each other in a first region than in a second region.

20. The guidewire in accordance with claim 19, wherein the wires have a cross section that is circular.

21. The guidewire in accordance with claim 19, wherein the wires have a cross section that is non-circular.

22. The guidewire in accordance with claim 19, wherein the wires a braided.

23. The guidewire in accordance with claim 19, wherein the first wire and the second wire are twisted about one another.

24. The guidewire in accordance with claim 19, wherein at least a portion of the wires are truncated.

25. The guidewire in accordance with claim 19, wherein the filler is comprised of stainless steel.

26. The guidewire in accordance with claim 19, wherein the filler is comprised of glass.

27. The guidewire in accordance with claim 19, wherein the filler is comprised of a polymer.

28. The guidewire in accordance with claim 19, wherein the filler is comprised of a carbon fibers.

29. The guidewire in accordance with claim 19, wherein the matrix is comprised of epoxy.

30. The guidewire in accordance with claim 19, further comprising a catheter having a lumen, wherein the shaft is disposed within the lumen.

31. The guidewire in accordance with claim 19, wherein the shaft includes a proximal region, a distal region, and a linking region.

32. The intravascular guidewire of claim 19, wherein the proximal section of the matrix is stiffer than the distal section of the matrix.

33. An intravascular guidewire, comprising:
an elongate shaft having an outside diameter;
wherein the shaft includes a filler and a polymeric matrix;
wherein the filler includes a plurality of wires;
wherein the matrix substantially surrounds the filler;
wherein the matrix includes an ultraviolet-curable adhesive;
wherein the outside diameter of the shaft is sized appropriately for being disposed within a lumen of an intravascular catheter; and
wherein each of the wires has a length and wherein the material composition of the wires changes along the length;
wherein the plurality of wires are more closely associated with each other in a first region than in a second region.

34. The intravascular guidewire of claim 33, wherein at least one of the wires has a proximal section and a distal section, and wherein the distal section includes a polymer.

35. The intravascular guidewire shaft of claim 34, wherein the proximal section includes a metal.

* * * * *